United States Patent

Fuchs et al.

[11] 4,287,208
[45] Sep. 1, 1981

[54] COMBATING ARTHROPODS WITH STEREOISOMERS OF 2,2-DIMETHYL-3-(2,2-DICHLOROVINYL)-CYCLOPROPANE-1-CARBOXYLIC ACID α-CYANO-3-PHENOXY-4-FLUORO-BENZYL ESTER

[75] Inventors: Rainer Fuchs, Wuppertal; Ingeborg Hammann, Cologne; Bernhard Homeyer, Leverkusen; Wolfgang Behrenz, Overath; Wilhelm Stendel, Wuppertal, all of Fed. Rep. of Germany

[73] Assignee: Bayer Aktiengesellschaft, Leverkusen, Fed. Rep. of Germany

[21] Appl. No.: 165,927

[22] Filed: Jul. 3, 1980

[30] Foreign Application Priority Data

Jul. 18, 1979 [DE] Fed. Rep. of Germany ....... 2928986

[51] Int. Cl.³ .................... A01N 53/00; C07C 121/75
[52] U.S. Cl. ............................... 424/304; 260/465 D; 260/465 F
[58] Field of Search .................... 260/465 D; 424/304

[56] References Cited

U.S. PATENT DOCUMENTS

| 4,146,554 | 3/1979 | Leigh ............................ 260/465 D |
| 4,218,469 | 8/1980 | Fuchs et al. ..................... 424/304 |

Primary Examiner—Dolph H. Torrence
Attorney, Agent, or Firm—Sprung, Felfe, Horn, Lynch & Kramer

[57] ABSTRACT

An arthropodicidally active substantially pure stereoisomer of 2,2-dimethyl-3-(2,2-dichlorovinyl)-cyclopropane-1-carboxylic acid α-cyano-3-phenoxy-4-fluoro-benzyl ester of the formula

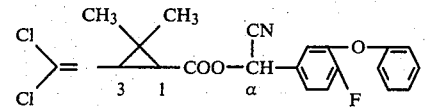

selected from the group consisting of ester in which the asymmetric C atoms , , and α have the following configuration:

| Isomer | Absolute configuration at the center | | |
|---|---|---|---|
| | 1 | 3 | α |
| a | R | R | R |
| b | R | R | S |
| c | R | S | R |
| d | R | S | S |
| e | S | S | S |
| f | S | S | R |
| g | S | R | S |
| h | S | R | R, | and diastereomeric mixtures of (1R)-cis- and (1R)-trans-2,2-dimethyl-3-(2,2-dichlorovinyl)-cyclopropane-1-carboxylic acid (R,S)-α-cyano-3-phenoxy-4-fluoro-benzyl esters of the formula

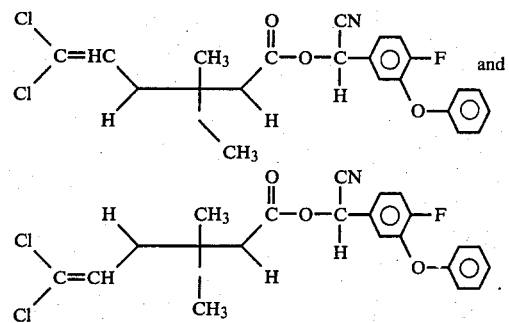

10 Claims, No Drawings

COMBATING ARTHROPODS WITH STEREOISOMERS OF 2,2-DIMETHYL-3-(2,2-DICHLOROVINYL)-CYCLOPROPANE-1-CARBOXYLIC ACID α-CYANO-3-PHENOXY-4-FLUORO-BENZYL ESTER

The invention relates to certain new stereoisomers of 2,2-dimethyl-3-(2,2-dichloro-vinyl)-cyclopropane-1-carboxylic acid α-cyano-3-phenoxy-4-fluoro-benzyl ester, to a process for their preparation and to their use as arthropodicides, especially as insecticides and acaricides.

It is already known that mixtures of the (±)-cis- and (±)-trans-forms of 2,2-dimethyl-3-(2,2-dichlorovinyl)-cyclopropane-1-carboxylic acid (±)-α-cyano-3-phenoxy-4-fluoro-benzyl ester have an insecticidal and acaricidal action (see DE-OS (German Published Specification) No. 2,709,264).

The present invention now provides, as new compounds, the single stereoisomers of 2,2-dimethyl-3-(2,2-dichlorovinyl)cyclopropane-1-carboxylic acid α-cyano-3-phenoxy-4-fluorobenzyl ester of the general formula

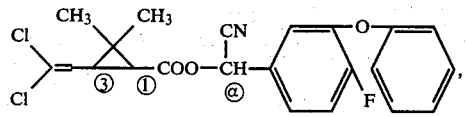

in which the asymmetric C atoms ①, ③ and @ have the following configuration:

| Isomer | Absolute configuration at the center | | |
|---|---|---|---|
|  | 1 | 3 | α |
| (a) | R | R | R |
| (b) | R | R | S |
| (c) | R | S | S |
| (d) | R | S | R |
| (e) | S | S | S |
| (f) | S | S | R |
| (g) | S | R | S |
| (h) | S | R | R. |

The invention also provides, as new diastereomeric mixture, the (1R)-cis-2,2-dimethyl-3-(2,2-dichlorovinyl)-cyclopropane-1-carboxylic acid (R,S)-α-cyano-3-phenoxy-4-fluoro-benzyl esters of the formulae (IIa) and cis

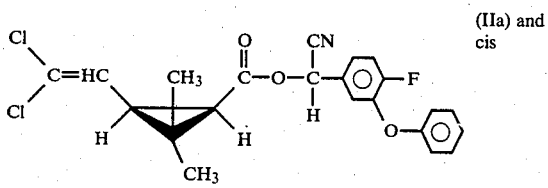

and the diastereomeric mixture of (1R)-trans-2,2-dimethyl-3-(2,2-dichlorovinyl)-cyclopropane-1-carboxylic acid-(R,S)-α-cyano-3-phenoxy-4-fluoro-benzylesters.

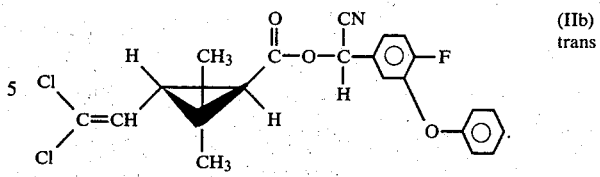

Isomers a-d of the formula (I) are particularly preferred.

The invention also provides a process for the preparation of a stereoisomer of the formula (I) with a configuration indicated under a-h, in which the acid chloride having the corresponding configuration is reacted with the alcohol having the corresponding configuration, in the presence of an acid-binding agent and, if appropriate, in the presence of a diluent.

The stereoisomers can also be obtained by subjecting the stereoisomer mixtures of the esters of the formula (I) to separation methods which are in themselves known (such as are described, for example, in Pestic. Sci. 1978, 9, pages 105–111). The compounds of the formulae (IIa) and (IIb) are obtainable by reacting the acid chlorides having the corresponding configuration with the stereoisomer mixture of (R,S)-α-cyano-3-phenoxy-4-fluorobenzyl alcohol.

A compound of the formula (IIa) or (IIb) is also obtained when (1R)-cis- or (1R)-trans-2,2-dimethyl-3-(2,2-dichlorovinyl)-cyclopropane-1-carboxylic acid chloride of the formula

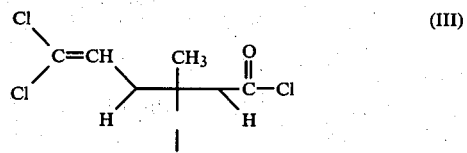

or

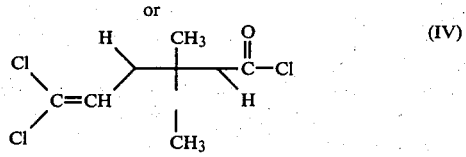

is reacted with 3-phenoxy-4-fluoro-benzaldehyde of the formula

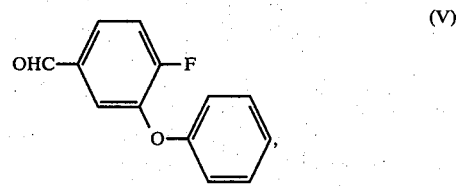

in the presence of at least an equimolar amount of an alkali metal cyanide, if appropriate in the presence of a catalyst and if appropriate using a diluent, as a temperature between 0° and 100° C.

The new stereoisomers of the formula (I) with the configurations indicated under a–h, preferentially the isomers Ia-d, but especially the isomers b and c, and the (1R)-cis and (1R)-trans-2,2-dimethyl-3-(2,2-dichlorovinyl)-cyclopropane-1-carboxylic acid (R,S)-α-cyano-3-phenoxy-4-fluoro-benzyl esters of the formulae (IIa)

and (IIb) are distinguished by a particularly high insecticidal and acaricidal activity.

Surprisingly, the new compounds exhibit a considerably more powerful insecticidal and acaricidal action than the isomer mixtures of 2,2-dimethyl-3-(2,2-dichlorovinyl)-cyclopropane-1-carboxylic acid α-cyano-3-phenoxy-4-fluoro-benzyl ester which are known from the state of the art. The individual stereoisomers display a different spectrum of action.

The reaction which proceeds in the preparation of the stereoisomers of the formula (I) can be represented, for example, by the following equation:

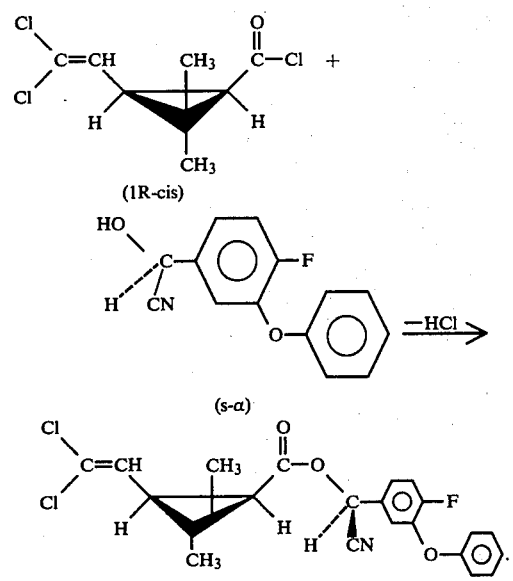

The remaining isomers of the formula (I) are prepared analogously.

The compounds of the formulae (IIa) and (IIb) can also be prepared in this manner if, instead of the individual stereoisomeric alcohols, the racemic mixture (R,S) of the alcohol is used.

The reaction which proceeds in the preparation of the new compound of the formula (IIa) can be represented by the following equation

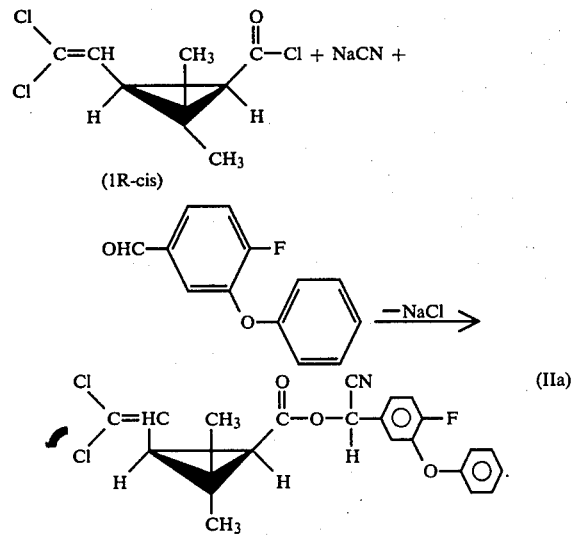

The compound of the formula (IIb) is prepared analogously.

The (1R)-cis- or (1R)-trans-2,2-dimethyl-3-(2,2-dichloro-vinyl)-cyclopropane-1-carboxylic acid chloride (III) or (IV) to be used as the starting compound can be prepared from the known (1R)-cis- or (1R)-trans-2,2-dimethyl-3-(2,2-dichloro-vinyl)-cyclopropane-1-carboxylic acid [=(±)-cis or (+)-trans-2,2-dimethyl-3-(2,2-dichlorovinyl)-cyclopropane-1-carboxylic acid (see Pestic. Sci. 1974, 5, 791–799)] by customary methods, for example by reaction with thionyl chloride, if appropriate in the presence of a diluent, for example carbon tetrachloride, at temperatures between 10° and 100° C.

The 3-phenoxy-4-fluoro-benzaldehyde (V) to be employed as a further starting compound is known (see DE-OS (German Published Specification) No. 2,709,264).

Alkali metal cyanides which are employed for the preparation of the new compounds are, preferably, sodium cyanide and potassium cyanide.

The R-α-cyano-3-phenoxy-4-fluoro-benzyl and S-α-cyano-3-phenoxy-4-fluorobenzyl alcohols to be used as starting materials for the preparation of the compounds of the formula (I) with the configurations indicated under a-h have not been disclosed in the literature hitherto. S-α-cyano-3-phenoxy-4-fluoro-benzyl alcohol is prepared, for example, by a process analogous to that described in DE-OS (German Published Specification) No. 2,902,466 for the preparation of S-α-cyano-3-phenoxy-benzyl alcohol, by reacting (R,S)-α-cyano-3-phenoxy-4-fluoro-benzyl alcohol with the lactone of cis-2,2-dimethyl-3S-(dihydroxy-methyl)-cyclopropane-1R-carboxylic acid in the presence of an acid agent, separating the resulting diastereomer mixture by chromatography and hydrolyzing the resulting (1R,5S)-6,6-dimethyl-(4R)-[(S)-cyano-(3'-phenoxy-4-fluoro-phenyl)-methoxy]-3-oxa-bicyclo[2.1.0]hexan-2-one under acid conditions to give S-α-cyano-3-phenoxy-4-fluorobenzyl alcohol.

R-α-Cyano-3-phenoxy-4-fluorobenzyl alcohol is prepared analogously.

The (R,S)-α-cyano-3-phenoxy-4-fluorobenzyl alcohol to be employed as the starting material is known (see DE-OS (German Published Specification) No. 2,709,264).

The process for the preparation of the new compounds (I) and (IIa) and (IIb) is preferably carried out using a diluent. Possible diluents are virtually any of the inert organic solvents. These include, as preferences, aliphatic and aromatic, optionally chlorinated hydrocarbons, such as pentane, hexane, heptane, cyclohexane, benzene, toluene, xylene, methylene chlorine, chloroform, carbon tetrachloride, chlorobenzene and o-dichlorobenzene; ethers, such as diethyl ether, dibutyl ether, tetrahydrofuran and dioxane; ketones, such as acetone, methyl ethyl ketone, methyl isopropyl ketone and methyl isobutyl ketone; and nitriles, such as acetonitrile and propionitrile.

Of the above-mentioned solvents, those which are water-immiscible are preferably used, in combination with water as a second solvent component, that is to say the process is carried out in a two-phase medium.

In this case, compounds which are customarily used as auxiliaries for the phase transfer of reactants in reactions in multi-phase media can be employed as catalysts. Tetraalkyl- and trialkylaralkyl-ammonium salts, for example tetrabutylammonium bromide, methyltrioctylammonium chloride and trimethylbenzylammonium hydrogen sulphate, may be mentioned in particular.

The reaction temperature is in general kept between 0° and 100° C., preferably between 10° to 50° C. The preparative process is usually carried out under normal pressure.

The starting substances are usually employed in equimolar amounts for carrying out the process according to the invention. An excess of one or the other of the reactants provides no substantial advantages. The reaction is in general carried out in suitable diluents, if appropriate in the presence of a catalyst, and the reaction mixture is stirred at the required temperature for several hours. Thereafter, an organic solvent, for example toluene, is added and the organic phase is worked up in the customary manner, by washing and drying and distilling off the solvent.

The new compounds of the formula (I) and (IIa and b) are obtained in an oily form and cannot be distilled without decomposition, but are freed from the last volatile constituents by so-called "incipient distillation", that is to say by prolonged heating to moderately elevated temperatures under reduced pressure, and are purified in this manner. They are characterized by their $^1$H—NMR spectrum.

As already mentioned, the new stereoisomers of the formula (I) with the configurations indicated under a–h, especially Ia–Id, and the (1R)-cis- and (1R)-trans-2,2-dimethyl-3-(2,2-dichlorovinyl)-cyclopropane-1-carboxylic acid (R,S)-α-cyano-3-phenoxy-4-fluoro-benzyl esters (I) are distinguished by a high insecticidal and acaricidal activity.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec. ;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratoriodes, Melanoplus differentials* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Marcrosiphum avenae,* Myzus spp., *Phorodon humuli, Rhopalosiphum padi,* Empoasca spp., *Euscelis bilobatus, Nephotettix cincticeps, Lecanium cornia, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as actone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.0001–10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The active compounds according to the invention are also suitable for combating ectoparasites and endoparasites in the field of veterinary medicine.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal composition containing an active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects or acarids which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects or acarids by the application to said animals of a compound according to the present invention, in admixture with a diluent or carrier.

PREPARATIVE EXAMPLES

EXAMPLE 1

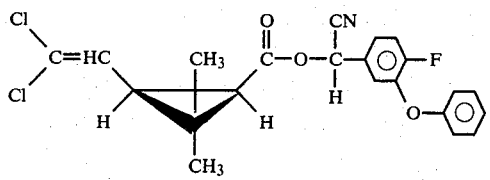
(1)

20.9 g (0.0967 mol) of 3-phenoxy-4-fluoro-benzaldehyde and 22.0 g (0.0967 mol) of (1R)-cis-2,2-dimethyl-3-(2,2-dichloro-vinyl)-cyclopropanecarboxylic acid chloride were added dropwise to a mixture of 7.5 g of sodium cyanide, 11.5 ml of water, 300 ml of n-hexane and 2.5 g of tetrabutylammonium bromide at 20°–25° C., while stirring, and the mixture was then stirred at 20°–25° C. for 4 hours. 400 ml of toluene were then added to the reaction mixture and the mixture was twice extracted by shaking with 300 ml of water each time. The organic phase was separated off and dried over magnesium sulphate and the solvent was distilled off under a waterpump vacuum. Last residues of solvent were removed by subjecting the mixture to brief incipient distillation at a bath temperature of 60° C./1 mm Hg. 37.4 g (89.1% of theory) of (1R)-cis-2,2-dimethyl-3-(2,2-dichlorovinyl)-cyclopropanecarboxylic acid (R,S)-α-cyano-3-phenoxy-4-fluoro-benzyl ester were obtained as a viscous oil with a specific optical rotation $[α]_D^{20} = +7.7°$ (c=2.0 in CHCl$_3$).

$^1$H—NMR spectrum (CDCl$_3$/TMS), δ (ppm): Dimethyl-H: 1.0–1.3 (m/6H); cyclopropane-H: 1.68–2.25 (m/2H); vinyl-H: 6.08 (d,/1H); benzyl-H: 6.21 (S/½H) and 6.26 (S/½H); and aromatic-H: 6.8–7.5 (m/8H).

EXAMPLE 2

The compound (1R)-trans-2,2-dimethyl-3-(2,2-dichlorovinyl)-cyclopropane-carboxylic acid (R,S)-α-cyano-3-phenoxy-4-fluoro-benzyl ester, of the formula

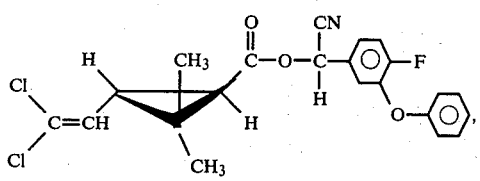
(2)

was obtained in a manner analogous to that described in Example 1. $[α]_D^{20} = -8.7°$ (c=2.0 in CHCl$_3$).

$^1$H-NMR spectrum (CDCl$_3$/TMS), τ (ppm): Aromatic-H: 2.43–3.17 (m/8H); benzyl-H: 3.64 (S/½H) and 3.67 (S/½H); vinyl-H: 4.38 (α/½ H) and 4.41 (α/½ H); cyclopropane-H: 7.53–8.5 (m/2H); and dimethyl-H: 8.6–8.9 (m/6H).

EXAMPLE 3

(1S)-cis-2,2-dimethyl-3-(2,2-dichloro-vinyl)-cyclopropanecarboxylic acid (R,S)-α-cyano-3-phenoxy-4-fluorobenzyl ester, of the formula

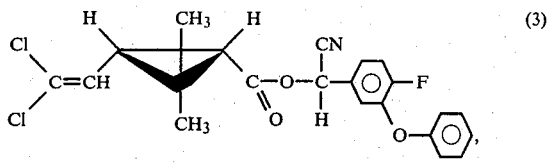
(3)

was obtained in a manner analogous to that described in Example 1.

EXAMPLE 4

Separation of the α-R and α-S diastereomers of 1-R-esters (a) 10 g of cis-3-(2,2-dichlorovinyl)-2,2-dimethyl-cyclopropane-1R-carboxylic acid α-(R,S)-cyano-3-phenoxy-4-fluoro-benzyl ester were subjected to preparative high pressure liquid chromatography.

Column: 23.4 mm×250 mm, 7 μm silica gel.
Mobile phase: 48% of n-hexane, 47% of cyclohexane and 5% of diethyl ether.
Amount flowing through: 30 ml/minute
Amount applied: 100 mg
Separation time: Fraction I: 8.5 minutes; Fraction II: 9.5 minutes.

The two fractions were then freed from solvent in vacuo.

As Fraction I, 1.6 g of cis-3-(2,2-dichloro-vinyl)-2,2-dimethyl-cyclopropane-1R-carboxylic acid α-(R)-cyano-3-phenoxy-4-fluoro-benzyl ester were obtained as a colorless oil.

$[α]_D^{20} = -15.0°$ (c=1.0 in CHCl$_3$). $^1$H-NMR spectrum (CDCl$_3$/TMS) τ (ppm): —CHCN: 3.72 (S/1H);

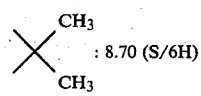 : 8.70 (S/6H)

As Fraction II, 1.5 g of cis-3-(2,2-dichloro-vinyl)-2,2-dimethyl-cyclopropane-1R-carboxylic acid α-(S)-cyano-3-phenoxy-4-fluoro-benzyl ester were obtained as colorless crystals with a melting point of 50°–52° C.
$[α]_D^{20} = +24.5°$ (c=1.0 in CHCl$_3$).
$^1$H-NMR spectrum (CDCl$_3$/TMS), τ (ppm)—CHCN: 3.68 (s/1H);

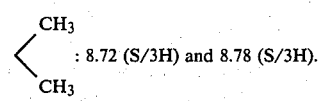 : 8.72 (S/3H) and 8.78 (S/3H).

(4b) In a manner analogous to that described in Example 4a.

8 g trans-3-(2,2-dichlorovinyl)-2,2-dimethyl-cyclopropane-1R-carboxylic acid α-(R,S)-cyano-3-phenoxy-4-fluoro-benzyl ester were subjected to preparative high pressure liquid chromatography.

As Fraction I, 0,9 g trans-3-(2,2-dichloro-vinyl-)-2,2-dimethyl-cyclopropane-1R-carboxylic acidα-(R)-cyano-3-phenoxy-4-fluoro-benzyl ester were obtained.

As Fraction II, 0.6 g trans-3-(2,2-dichloro-vinyl)-2,2-dimethyl-cyclopropane-1R-carboxylic acidα-(S)-cyano-3-phenoxy-4-fluoro-benzyl ester were obtained as colorless crystals (from m-hexane) with a melting point of 68°–69° C.

$[α]_D^{20} = -2,1°$ (C=1,0 in CHCl$_3$).

1HNMR spectrum (CDCl3/TMS), τ (ppm):—CHCN: 3,65 (S/1H); vinyl-H: 4,39 (d/1H);

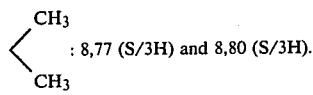 : 8,77 (S/3H) and 8,80 (S/3H).

The pesticidal activity of the compounds of this invention is illustrated by the following examples wherein the compounds according to the present invention are each identified by the number (given in brackets) from Examples 1 to 4 hereinabove:

EXAMPLE 5

Test insects: *Sitophilus granarius*
Number of test insects: 25
Solvent: Acetone The active compound was taken up in the solvent at a rate of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test insects was then placed in the Petri dish and the dish was covered with a glass lid.

The condition of the test insects was observed 3 days after the commencement of the experiments. The destruction, in %, was determined. 100% denoted that all of the test insects had been killed; 0% denoted that none of the test insects had been killed.

In this test, for example, the following compound showed a superior action compared with the prior art: (1).

EXAMPLE 6

Test insects: *Muscasca domestica* (resistant) *Aedes aegypti*
Number of test insects: 25 in each case
Solvent: Acetone The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test insects was then placed in the Petri dish and the dish was covered with a glass lid.

The condition of the test insects was continuously observed. The time which was necessary for 100% "knock-down" was determined.

In this test, for example, the following compounds showed a superior action compared with the prior art: (1) and (2).

EXAMPLE 7

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

In this test, for example, the following compounds showed a superior action compared with the prior art: (1) and (2).

EXAMPLE 8

Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

In this test, for example, the following compounds showed a superior action compared with the prior art: (1) and (2).

EXAMPLE 9

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration Bean plants (*Phaseolus vulgaris*) which were heavily infested with the two-spotted spider mite (*Tetranychus urticae*) in all stages of development were treated by being dipped into the preparation of the active compound.

After the specified periods of time, the degree of destruction was determined as a percentage: 100% meant that all of the spider mites were killed whereas 0% meant that none of the spider mites were killed.

In this test, for example, the following compound showed a superior activity compared with the prior art: (1).

EXAMPLE 10

Test with Lucilia cuprina res. larvae
Solvent: 35 parts by weight of ethylene glycol monomethyl ether; 35 parts by weight of nonylphenol polyglycol ether To produce a suitable preparation of active compound, three parts by weight of active compound were mixed with seven parts by weight of the above-mentioned solvent mixture and the concentrate thus obtained was diluted with water to the particular desired concentration.

About 20 *Lucilia cuprina* res. larvae were introduced into a test tube which contained about 1 cm³ of horse muscle and 0.5 ml of the preparation of active compound. After 24 hours, the degree of destruction was determined.

In this test, for example, the following compound showed a superior action compared with the prior art: (1).

EXAMPLE 11

Test with *Boophilus microplus* resistant
Solvent: 35 parts by weight of ethylene glycol monomethyl ether, 35 parts by weight of nonylphenol polyglycol ether To produce a suitable preparation of active compound, three parts by weight of active compound were mixed with seven parts by weight of the solvent mixture indicated above, and the concentrate thus obtained was diluted with water to the desired concentration.

10 adult *Boophilus microplus* res. were immersed for 1 minute in the active compound preparation to be tested. After transfer to plastic beakers and storage in a climatically controlled chamber, the degree of destruction was determined.

In this test, for example, the following compound showed a superior action compared with the prior art: (1).

EXAMPLE 12

Plutella test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were treated by being dipped into a preparation of active compound and were infested with caterpillars of the diamond-back moth (*Plutella maculipennis*), as long as the leaves were still moist.

After the specified periods of time, the degree of destruction was determined as a percentage: 100% meant that all of the caterpillars were killed whereas 0% meant that none of the caterpillars were killed.

In this test, for example, the following compound showed a superior activity compared with the prior art: (2).

EXAMPLE 13

Laphymga test
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cabbage leaves (*Brassica oleracea*) were treated by being dipped into the preparation of active compound of the desired concentration and were infested with caterpillars of the owlet moth (*Laphymga frugiperda*), as long as the leaves were still moist.

After the specified periods of time, the destruction in % was determined. 100% meant that all of the caterpillars had been killed whereas 0% indicated that none of the caterpillars had been killed.

In this test, for example, the following compound showed a superior activity compared with the prior art: (1).

It will be appreciated that the instant specification and examples are set forth by way of illustration and not limitation, and that various modifications and changes may be made without departing from the spirit and scope of the present invention.

We claim:

1. A substantially pure stereoisomer of 2,2-dimethyl-3-(2,2-dichlorovinyl)-cyclopropane-1-carboxylic acid α-cyano-3-phenoxy-4-fluorobenzyl ester of the formula

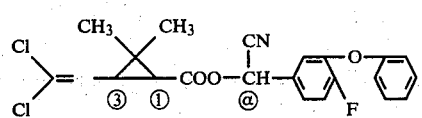

selected from the group consisting of esters in which the asymmetric C atoms ①, ③, and @ have the following configuration:

| Isomer | Absolute configuration at the center | | |
|---|---|---|---|
| | 1 | 3 | α |
| a | R | R | R |
| b | R | R | S |
| c | R | S | R |
| d | R | S | S |
| e | S | S | S |
| f | S | S | R |
| g | S | R | S |
| h | S | R | R, | the diastereomeric mixture of (1R)-cis-2,2-dimethyl-3-(2,2-dichlorovinyl)-cyclopropane-1-carboxylic acid (R,S)-α-cyano-3-phenoxy-4-fluoro-benzyl esters of the formula

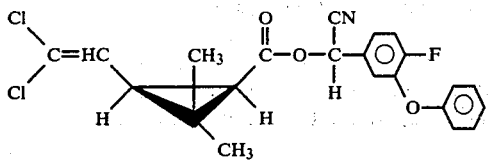

and the diastereomeric mixture of (1R)-trans-2,2-dimethyl-3-(2,2-dichlorovinyl)-cyclopropane-1-carboxylic acid (R,S)-α-cyano-3-phenoxy-4-fluoro-benzylesters of the formula

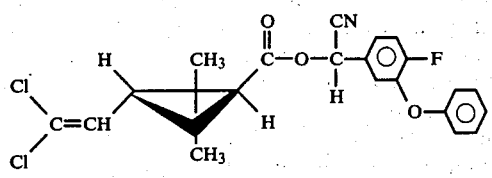

2. A substantially pure compound according to claim 1, wherein such compound is (1R, 3R)-2,2-dimethyl-3-(2,2-dichlorovinyl)-cyclopropanecarboxylic acid (R)-α-cyano-3-phenoxy-4-fluoro-benzyl ester.

3. A substantially pure compound according to claim 1, wherein such compound is (1R, 3R)-2,2-dimethyl-3-(2,2-dichlorovinyl)-cyclopropanecarboxylic acid (S)-α-cyano-3-phenoxy-4-fluoro-benzyl ester.

4. A substantially pure compound according to claim 1, wherein such compound is (1R, 3S)-2,2-dimethyl-3-(2,2-dichlorovinyl)-cyclopropanecarboxylic acid (R)-α-cyano-3-phenoxy-4-fluorobenzylester.

5. A substantially pure compound according to claim 1, wherein such compound is (1R, 3S)-2,2-dimethyl-3-(2,2-dichlorovinyl)-cyclopropanecarboxylic acid (S)-α-cyano-3-phenoxy-4-fluoro-benzylester.

6. A substantially pure compound according to claim 1, comprising a diastereomeric mixture of (1R, 3R)-2,2-dimethyl-3-(2,2-dichlorovinyl)-cyclopropanecarboxylic acid (R)-α-cyano-3-phenoxy-4-fluorobenzyl ester and (1R, 3R)-2,2-dimethyl-3-(2,2-dichlorovinyl)-cyclopropanecarboxylic acid (S)-α-cyano-3-phenoxy-4-fluoro-benzyl ester.

7. A substantially pure compound according to claim 1, comprising a diastereomeric mixture of (1R, 3S)-2,2-dimethyl-3-(2,2-dichlorovinyl)-cyclopropanecarboxylic acid (R)-α-cyano-3-phenoxy-4-fluorobenzylester and (1R, 3S)-2,2-dimethyl-3-(2,2-dichlorovinyl)-cyclopropanecarboxylic acid S-α-cyano-3-phenoxy-4-fluorobenzylester.

8. An arthropodical composition comprising an arthropodically effective amount of a substantially pure compound according to claim 1 in admixture with a diluent.

9. A method of combating arthropods which comprises applying to the arthropods, or to a habitat thereof, an arthropodicidally effective amount of a substantially pure compound according to claim 1.

10. The method according to claim 9, wherein the compound is (1R, 3R)-2,2-dimethyl-3-(2,2-dichlorovinyl)-cyclopropanecarboxylic acid (R)-α-cyano-3-phenoxy-4-fluorobenzyl ester, (1R, 3R)-2,2-dimethyl-3-(2,2-dichlorovinyl)-cyclopropanecarboxylic acid (S)-α-cyano-3-phenoxy-4-fluoro-benzyl ester, (1R, 3S)-2,2-dimethyl-3-(2,2-dichlorovinyl)-cyclopropanecarboxylic acid (R)-α-cyano-3-phenoxy-4-fluorobenzylester, and (1R, 3S)-2,2-dimethyl-3-(2,2-dichlorovinyl)-cyclopropanecarboxylic acid (S)-α-cyano-3-phenoxy-4-fluorobenzylester, a diastereomeric mixture of (1R, 3R)-2,2-dimethyl-3-(2,2-dichlorovinyl)-cyclopropanecarboxylic acid (R)-α-cyano-3-phenoxy-4-fluoro-benzyl ester and (1R, 3R)-2,2-dimethyl-3-(2,2-dichlorovinyl)-cyclopropanecarboxylic acid (S)-α-cyano-3-phenoxy-4-fluoro-benzyl ester, or a diastereomeric mixture of (1R, 3S)-2,2-dimethyl-3-(2,2-dichlorovinyl)-cyclopropanecarboxylic acid (R)-α-cyano-3-phenoxy-4-fluoro-benzylester and (1R, 3S)-2,2-dimethyl-3-(2,2-dichlorovinyl)-cyclopropanecarboxylic acid (S)-α-cyano-3-phenoxy-4-fluoro-benzylester, and is applied to a domesticated animal.

* * * * *